US006309655B1

(12) United States Patent
Minnix

(10) Patent No.: US 6,309,655 B1
(45) Date of Patent: Oct. 30, 2001

(54) SELF-INDICATING COSMETIC COMPOSITION

(75) Inventor: Cindy Minnix, Batavia, OH (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 09/302,264

(22) Filed: Apr. 30, 1999

(51) Int. Cl.$^7$ ................................. A61K 9/10; A61K 7/48
(52) U.S. Cl. .......................... 424/401; 510/130; 510/418; 514/844; 514/846
(58) Field of Search ....................................... 424/409, 401; 514/846, 844; 510/130, 137, 418, 419, 475, 511

(56) References Cited

U.S. PATENT DOCUMENTS 6,045,813 * 4/2000 Ferguson et al. .
6,063,366 * 5/2000 Suga et al. .

* cited by examiner

Primary Examiner—Edward J. Webman
(74) Attorney, Agent, or Firm—Piper Marbury; Rudnick & Wolfe LLP; Steven B. Kelber

(57) ABSTRACT

Disclosed herein is a cosmetic composition comprising a self-heating component, self-indicating disintegrating granules comprised of water-insoluble polymer and a colorant, which gives users indications of the length of time the composition has been applied and the degree of mixing when in use.

20 Claims, No Drawings

SELF-INDICATING COSMETIC COMPOSITION

BACKGROUND OF THE INVENTION

1. Field of the Invention

The present invention relates to a self-heating, self-indicating cosmetic composition which gives users indications of the length of time of application, location of effective application and the degrees of mixing and scrubbing when in use.

2. Description of the Background Art

Facial masks are products which are designed to provide a different type of cleansing effect than that which can be achieved with ordinary cleansing compositions. In this context, an ordinary cleansing composition is one which consists primarily of surfactants and emollients delivered from an aqueous vehicle. Ordinary cleansers remove dirt and soils, especially oily soils, by two primary mechanisms. The first, which is typical for foaming cleansers, including bar soaps, cleans the skin by a detergent effect obtained by the use of surfactants. The second mechanism, which is typical for non-foaming cleansers such as "cold cream", depends on a solvent effect whereby various emollients in the composition dissolve and lift up soils from the skin. Such compositions, together with the suspended soils are then removed by wiping the composition off with a tissue, or by similar means.

Facial masks can be classified as being of two general types. The first type is a "peel-off" mask which consists of a polymer, typically polyvinyl alcohol, in an aqueous or hydroalcoholic solution. These compositions are applied to the skin and allowed to dry. As the water and/or alcohol dries, the polymer forms a film which adheres to the surface of the skin. This film is then peeled off the skin, removing top layers of the skin together with any dirt of soil which may be present on the skin surface. The second type of mask is the "rinse-off" type. Rinse-off masks typically contain some type of finely-divided particles which are able, presumably due to their large surface area, to adsorb oily soils, particularly sebum. The most common type of powders used in rinse-off masks are clays, and the clays are typically suspended in an aqueous vehicle. The composition is applied to the skin and allowed to dry. Then the dried "cake", together with the adsorbed oil is removed from the skin by rinsing.

A problem observed with moisturizing compositions is that many components typically found in a moisturizing composition are a solid at or near room temperature, which can present difficulties in terms of penetration and distribution. Moisturizing compositions are generally formulated as an aqueous emulsion, however, a problem with emulsion delivery systems is that the presence of large amounts of water decreases the effectiveness of delivery of the moisturizing components. Pre-heating of the composition to provide a hot facial moisturizer may be conducted by conventional heat transfer methods, however such a heating is not always convenient and significantly complicates the moisturizing process.

In order to formulate a personal care composition which is "self-warming", the combination of an activated zeolite and anhydrous liquid vehicle has been reported (U.S. Pat. No. 4,626,550). The addition of a "self-warming" component to a rinse off cleansing mask composition provides for more effective sebum removal and an improved sensation during use. However, some self-warming zeolite materials provide for a composition of high alkalinity (as high as pH 12), such that it is desirable to minimize exposure time with the skin. A contact time ranging from 1–2 minutes is preferable. However in use, it is not always convenient to accurately measure time such that over exposure is a concern. In addition, the user of a cleansing composition may over scrub or under scrub (e.g. no scrubbing), such that irritation and/or sub-optimum cleansing may occur.

Moreover, when using an anhydrous "self-warming" component, which liberates heat of hydration, the quality of the warming will in-part, depend on the effectiveness of mixing of the anhydrous "self-warming" component with water. If the water and anhydrous "self-warming" components are not thoroughly mixed, the rate and degree of hydration may be reduced, and therefore, both the rate of heating and temperature rise will be sub-optimal. However, when using cleansing and/or moisturizing compositions, it is very easy to leave regions in which ineffective mixing occurs, since it can be difficult for the user to identify regions which have been thoroughly mixed. Effective mixing when using a "self-warming" component is thus desirable.

Accordingly, a self-warming cosmetic composition which, in use, provides an indication of time of use, effective application, as well as degree of mixing and scrubbing, would be an improvement over existing technology.

SUMMARY OF THE INVENTION

The present invention is directed to a cosmetic composition which combines a warming effect, a mild abrasive effect and an indicator of effective application. The warming effect is desirable for a cleansing composition because it can help improve the transfer of sebum from the skin into the mask by reducing the viscosity of the sebum, thereby facilitating its transfer from the skin surface and perhaps even help sebum within the pores of the skin to flow to the surface where it can be removed. The mild abrasive effect aids cleaning performance by helping to loosen dead skin cells and soils adhering to the skin surface. The warming effect is desirable for a moisturizing composition, since it reduces the viscosity of the moisturizing components and therefore eases the application of the moisturizing composition. The indicator provides for a signal to the user of the proper length of time as well as an indication of effective mixing. Additionally, the warming and mild abrasive effects are seen by many consumers as pleasant sensations which contribute to the enjoyment of using such a product.

According to the present invention, there is thus provided a self-heating, self-indicating cosmetic composition comprising a self-warming component; self-indicating disintegrating granules comprising water-insoluble polymer and a colorant; and an anhydrous water-miscible vehicle.

According to another embodiment of the present invention is a cleansing facial mask composition comprising a self-warming component; self-indicating disintegrating granules comprising water-insoluble polymer and a colorant; and an anhydrous water-miscible vehicle.

According to another embodiment of the present invention is a cleansing body scrub composition comprising a self-warming component; self-indicating disintegrating granules comprising water-insoluble polymer and a colorant; and an anhydrous water-miscible vehicle.

According to another embodiment of the present invention is a cleansing foot scrub composition comprising a self-warming component; self-indicating disintegrating granules comprising water-insoluble polymer and a colorant; and an anhydrous water-miscible vehicle.

According to another embodiment of the present invention is a moisturizing facial mask composition comprising a self-warming component; self-indicating disintegrating granules comprising water-insoluble polymer and a colorant; and an anhydrous water-miscible vehicle.

Since the cosmetic composition according to the present invention contains a self-warming component and self-indicating disintegrating granules, a pleasant feeling upon use and an excellent effect for facilitating the circulation of the blood to improve a complexion, is obtained. The presence of a water soluble or water-dispersible colorant, which is released under the action of physical manipulation provides an indication of the degree of physical mixing, by color change.

DETAILED DESCRIPTION OF THE PREFERRED EMBODIMENTS

The warming effect of the present invention may be achieved by the use of a self-warming component which generates heat when brought into contact with water. The source of the heat is the release of hydration energy and the composition should be anhydrous before addition of the self-warming component, in order to prevent premature hydration of the self-warming component before the formula is applied. Several suitable heat-generating components are known to the art. These include various water-soluble, polyhydric alcohols such as glycerin and polyethylene glycol. A preferred heat-generating component is a zeolite, and in particular "Zeolite A". The zeolite is at least partially activated, such that the zeolite has the capacity to absorb water. Activation may be accomplished by conventional techniques known to those of ordinary skill in the art, such as by heating, optionally under reduced pressure. Suitable zeolites are typically available commercially in an activated form. The use of Zeolite A as a source of heat for topical compositions is disclosed in U.S. Pat. No. 4,379,143 (Sherry et al) and U.S. Pat. No. 4,626,550 (Hertzenberg), the relevant portions of which are hereby incorporated by reference.

The amount of self-warming component, is not particularly limited and will typically be an amount sufficient to produce a suitable temperature increase, when in use. When the self-warming component is a zeolite, the amount will generally range from 15–55 wt. %, preferably 20–50 wt. %, more preferably from 30–40 wt. %, based on the total weight of the composition.

The self-indicating disintegrating granules useful in the present invention are comprised of water-insoluble polymer and a colorant.

Examples of the water-insoluble polymer include organic high-molecular compounds such as polyethylene, polystyrene, polyester, polyvinyl chloride, polyamide, polypropylene, nylon, polyvinylidene fluoride, polyurethane, (meth)acrylic resins, (meth)acrylate resins, polysiloxane, crystalline cellulose, starch and derivatives thereof, biopolymers such as chitin, or ground shells, such as apricot, walnut and/or coconut shells; and inorganic powders such as silica, alumina, talc, kaolin, titanium oxide, zinc oxide, quartz, pumice and calcium phosphate powders. Preferably the water-insoluble primary particles are made of polyethylene or polymethacrylate copolymer.

The self-indicating disintegrating granules may take the form of an agglomeration of water-insoluble polymer primary particles, which may be in any form of a spherical form, an indeterminate form and the like. However, the spherical form is particularly preferred from the viewpoint of safety. As an agglomeration of water-insoluble polymer primary particles, the particle may be held together by a binder. The self-indicating disintegrating granules may also take the form of a water-insoluble polymer matrix in which the colorant is encapsulated or entrapped. In all cases, the self-indicating granules are readily friable, such that the physical manipulation of applying the cosmetic composition is sufficient to disintegrate the granules and release the colorant.

Examples of the binder include water-soluble binders such as organic high-molecular compounds such as ethyl cellulose, acetyl cellulose, nitrocellulose, hydroxymethyl cellulose, hydroxyethyl cellulose, hydroxypropyl cellulose, hydroxypropyl methylcellulose polyvinyl pyrrolidone, polyvinyl acetate and polyvinyl alcohol, and/or water-insoluble binders such as animal and plant oils which are solid at ordinary temperature, such as hydrogenated fish oil, hydrogenated castor oil and hydrogenated rapeseed oil. Of these, hydroxypropyl cellulose is particularly preferred. The selection of the amount of binder and, where applicable, the ratio of water-soluble binder to water insoluble binder is within the level of skill of those of ordinary skill in the art without undue experimentation. By adding water-soluble binder, the rate of colorant release over time, independent of physical manipulation, is increased, such that an exposure time indicating effect is amplified.

The colorant material contained in the self-indicating disintegrating granules is not particularly limited, provided that the colorant is water soluble or water-dispersible and non-staining. Suitable colorants should also provide a color, which when released, provides for effective color contrast from the color of the composition before use. Suitable colorants include pigments such as ultramarine, and $TiO_2$, iron oxide and chromium green and dyes such as any of the well known FD& C or D & C dyes. Mixtures of pigments, dyes and both are possible. In a preferred embodiment, the color may be ultramarine.

The amount of colorant contained within the self-indicating disintegrating granules is not particularly limited and will generally range from 0.1–35 wt. %, preferably from 1–15 wt. %, more preferably 8–11 wt. %, based on the total weight of the self-indicating disintegrating granules.

The self-indicating disintegrating granules of the agglomerate type are comprised of these water-insoluble primary particles, colorant and binder can be prepared by a general granulating process, for example, fluidized bed granulation, agitation granulation or extrusion granulation. In particular, they may preferably be prepared in accordance with a process in which primary particles, colorant, and binder are granulated. The ingredients which are to form the bead can be blended together with a suitable solvent to form a slurry or paste which is then dried to produce a solid material. This solid can then be chopped up or otherwise broken down mechanically to give the desired particle size. Another method involves dry-blending the ingredients for the beads in a dry state and forming beads via a granulation process.

The self-indicating disintegrating granules of the matrix type are comprised of water-insoluble polymer and colorant and can be prepared by polymerization of monomer and crosslinking agent in the presence of colorant, resulting in entrapment of colorant in the polymer. The colorant may be dispersed or solubilized in a vehicle, such as dimethicone. Suitable monomers will be recognized by those of ordinary skill in the art as suitable for the preparation of organic high-molecular compounds such as polyethylene, polystyrene, polyester, polyvinyl chloride, polyamide, polypropylene, nylon, polyvinylidene fluoride, polyurethane, (meth)acrylic resins, (meth)acrylate resins, polysiloxane, crystalline cellulose, starch and derivatives thereof. Suitable crosslinking agents may be selected based on the specific polymer and the method of polymerization, and is within the level of skill of those of ordinary skill in the art. By selection of the crosslinking monomer, monofluctional monomer, and ratio thereof the physical properties of the granules may be adjusted. By decreasing the amount of cross-linking monomer, a soft, highly disintegrateable material may be formed. Suitable methods are described in U.S. Pat. Nos. 4,724,240, 4,855,127 and 4,880,617, the relevant portions of which are hereby incorporated by reference.

A suitable disintegrating granule of the matrix type may also be formed by casting an emulsion of a continuous phase of water-insoluble polymer and a discontinuous phase of liquid material immiscible with said continuous phase of water-insoluble polymer, such that the liquid material has dispersed therein the colorant. Suitable liquid materials will depend upon the solvent for the water-insoluble polymer, however water and alcohol solvents will typically work with many solutions of water-insoluble polymer in organic solvents.

In order to provide a mild abrasive effect, the bead composition and processing is preferably done in such a way as to produce a relatively soft, friable bead that breaks down when rubbed on the skin. This will ensure that the bead will not scratch the skin, and will also release the colorant quickly as the inventive composition is rubbed onto wet skin.

Self-indicating disintegrating granules obtained by using polyethylene particles as the primary particles, and hydroxypropyl cellulose as the binder are preferred.

Colorant containing granules for use as self-indicating disintegrating granules of the agglomerate type are known in the cosmetic art (Ichimaru Pharcos Co. Ltd. of Japan, through U.S. Cosmetics). Suitable self-indicating granules of the matrix type may be purchased from Advanced Polymer Systems. These granules are highly crosslinked polymethacryate copolymer, in which up to 35% wt. % dimethicone may be entrapped. All or part of the dimethicone may be replaced by colorant.

After incorporated into a cosmetic composition, the thus-obtained self-indicating disintegrating granules in the cosmetic composition preferably have a compression strength of 0.002–0.1 kgf/mm$^2$, preferably 0.002–0.05 kgf/mm$^2$, more preferably 0.002–0.02 kgf/mm$^2$. If the compression strength is lower than 0.002 kg fmm$^2$, the resulting cosmetic composition neither gives users a pleasant feeling upon use nor has a sufficient effect for improving a complexion. If the compression strength is higher than 0.1 kgf/MM$^2$ on the other hand, the resulting cosmetic composition strongly gives users an irritated feeling and a feeling of physical disorder.

The compression strength is a value determined by taking a self-indicating disintegrating granule out of the cosmetic composition or a bulk of the feed stock with tweezers carefully so as not to damage it, placing it on a specimen carrier of a Micro Compression Testing Machine (manufactured by Shimadzu Corporation) and measuring its compression strength by a method known per se in the art.

The particle size of the self-indicating disintegrating granules (e.g. agglomeration of primary particles) in the cosmetic composition is preferably within a range of 100–2,000 $\mu$m, preferably 100–1,000 $\mu$m, more preferably 200–600 $\mu$m. When the granule size falls within this range, the resulting cosmetic composition has a sufficient effect for improving a complexion and gives users not too strong of an irritating feeling. It is hence preferable to use these self-indicating disintegrating granules having a particle size within such a range. The average particle size of the primary particles of the granules in the cosmetic composition is at most 100 $\mu$m, preferably 1–30 $\mu$m, more preferably 5–20 $\mu$m. If the average particle size exceeds 100 $\mu$m, the resulting cosmetic composition gives users a too strongly irritated feeling after disintegration of the granules. It is hence not preferable to contain any primary particles having such a great average particle size.

These self-indicating disintegrating granules may be used either singly or in any combination thereof and are preferably incorporated in a range of 0.1–5 wt. % (hereinafter indicated merely by "%"), more preferably 0.3–3%, most preferably 0.4–0.8% based on the total weight of the composition. Within these ranges of granule addition, the cosmetic composition has a sufficient effect for improving a complexion and give no feeling of physical disorder upon use. However, it will be appreciated by those of ordinary skill in the art, that the amount of granules added, will in-part depend upon the concentration of colorant therein, such that for granules containing a low concentration of colorant, the amount of granule may be increased, to provide for effective color change indication, while for high concentrations of colorant, the amount of granule may be decreased, while still providing effective color change indication. The adjustment of colorant concentration and granule loading in the composition is within the level of skill of those of ordinary skill in the art, without undue experimentation.

It is preferable that the cosmetic composition be anhydrous, which will be understood by those of skill in the cosmetic art to mean that water has not been added as a component. However, those of skill in the art will also appreciate that water may be present in the composition via its presence in the formulation components and absorption from the atmosphere. In a preferred embodiment, the amount of water, if any, is $\leq$5, wt. %, more preferably $\leq$2.5 wt. %, even more preferably $\leq$1.0 wt. %. It will also be understood that the composition contains, if any, an amount of water of $\leq$5.0%, $\leq$4.0%, $\leq$3.5%, $\leq$3.0%, $\leq$2.5%, $\leq$2.0%, $\leq$1.5%, $\leq$1.0%, $\leq$0.5%, $\leq$0.1%, $\leq$0.05%, and $\leq$0.001%, based on the total weight of the composition. The presence of water can act to deactivate the "self-heating" component, and reduce its effectiveness in warming the composition.

As the anhydrous water-miscible vehicle examples thereof include ethylene glycol, diethylene glycol, triethylene glycol and still higher polyethylene glycols; propylene glycol, dipropylene glycol and still higher polypropylene glycols; butylene glycols such as 1,3-butylene glycol and 1,4-butylene glycol; glycerol, diglycerol and still higher polyglycerols; sugar alcohols such as sorbitol, mannitol, xylitol and maltitol; adducts of glycerols with ethylene oxide (hereinafter abbreviated as "EO") or propylene oxide (hereinafter abbreviated as "PO"); adducts of sugar alcohols with EO or PO; monosaccharides such as galactose and fructose, and EO or PO addicts thereof; polysaccharides such as maltose and lactose, and EO or PO addicts thereof; sodium pyrrolidonecarboxylate; and polyoxyethylene methylglucosides (number of moles of EO added: 10, 20, etc.). Preferably the anhydrous water-miscible vehicle is butylene glycol. Applicants have also discovered, that for a water activated "self-heating" composition, butylene glycol formulations possess greater storage stability and retain a greater amount of heating capacity.

In the cosmetic compositions according to the present invention, ingredients commonly used in the classical external skin care compositions, skin cleansing compositions, primary particle abrasives, cosmetic compositions and massaging compositions, for example, oily substances, anti-melanogenic agents, sebum secretion inhibitors, blood circulation-facilitating agents, moisturizers, softeners, surfactants, keratin protecting agents, thickeners, antiseptics, pH adjusters, perfume bases antioxidants, colorants, medicinally-effective agents, solvents, and the like, may be suitably incorporated in addition to the above-described components so far as no detrimental influence is thereby imposed on the effects of the present invention. Suitable primary particle abrasives are the same materials described for the primary particles for the self-indicating disintegrating granules, however, the primary particle size may be adjusted by those of ordinary skill in the art to provide the desired level of abrasion.

Examples of the oily substances include isotridecyl isononanate, glyceryl tri-2-ethylhexanoate, neopentyl glycol dicaprate, 1-isostearoyl-3-myristoylglycerol, diisostearyl adipate, liquid isoparaffin, squalane, diglyceryl monoisostearate, diglyceryl diisostearate, diglyceryl triisostearate, glyceryl tri(caprylate caprate), isotridecyl myristate, octyldodecyl myristate, hexyldecyl myristate, octyldodecyl neodecanoate, evening primrose oil, jojoba oil, abocado oil, grape oil, turtle oil, mink oil, orange raffinate oil, polyoxyethylenemethyl polysiloxane copolymers, diglyceryl tetraisostearate, trimethylolpropane triisostearate, neopentyl glycol dioctanoate, diisostearyl malate, octyldodecyl lactate, 1,3-myristoylglycerol and isostearyl adipate.

These oily substances may be used either singly or in any combination thereof and are preferably incorporated in a proportion of 1–50%, particularly 3–17% based on the total weight of the composition.

The anti-melanogenic agents can serve to improve spots, freckles and a dark complexion caused by a melanin pigment, and as such agents, may be used, for example, ascorbic acid and derivatives thereof, hydroquinone derivatives, kojic acid and derivatives thereof, placenta extracts, plant extracts, and the like, which are printed in "Fragrance Journal, Extra Edition Vol. 14 (1995)" and are in common use as anti-melanogenic agents.

Specifically, examples of ascorbic acid and derivatives thereof include alkali metal salts of L-ascorbic acid phosphate such as sodium L-ascorbic acid phosphate and potassium L-ascorbic acid phosphate; alkaline earth metal salts of L-ascorbic acid phosphate such as magnesium L-ascorbic acid phosphate and calcium L-ascorbic acid phosphate; trivalent metal salts of L-ascorbic acid phosphate such as aluminum L-ascorbic acid phosphate; alkali metal salts of L-ascorbic acid sulfate such as sodium L-ascorbic acid sulfate and potassium L-ascorbic acid sulfate; alkaline earth metal salts of L-ascorbic acid sulfate such as magnesium L-ascorbic acid sulfate and calcium L-ascorbic acid sulfate; trivalent metal salts of L-ascorbic acid sulfate such as aluminum L-ascorbic acid sulfate; alkali metal salts of L-ascorbic acid such as sodium L-ascorbate and potassium L-ascorbate; alkaline earth metal salts of L-ascorbic acid such as magnesium L-ascorbate and calcium L-ascorbate; and trivalent metal salts of L-ascorbic acid such as aluminum L-ascorbate.

Examples of the hydroquinone derivatives include condensates of hydroquinone with a saccharide, such as arbutin, and condensates of an alkylhydroquinone obtained by introducing an alkyl group having 1–4 carbon atoms into hydroquinone with a saccharide.

Examples of kojic acid and derivatives thereof include kojic acid, monoesters such as kojic acid monobutyrate, kojic acid monocaprate, kojic acid monopalmitate, kojic acid monostearate, kojic acid monocinnamate and kojic acid monobenzoate, and diesters such as kojic acid dibutyrate, kojic acid dipalmitate, kojic acid distearate and kojic acid dioleate.

As the placenta extracts, may be used those generally sold as water-soluble placenta extracts and used as cosmetic raw materials. Examples thereof include those obtained by subjecting a placenta of a mammal such as bovine, swine or human to washing, depletion of blood, shredding, freezing and the like to extract a water-soluble component and then removing impurities from the water-soluble component.

Examples of the plant extracts include extracts from licorice, the root of kudzu, soybean, trillium, *Tulipa edulis, Anemarrhena asphodeloides* Bunge, *Ophiopogon japonicus* Ker-Gawler, sansevieria, white oak, *Artemisia capillaris Thunb*, chamomile, artichoke, aster, rice, clove, turmeric, balsam pear, aloe, tea plant, creeping saxifrage, *Scutellariae radix*, loquat, orange peel, ginseng, althea, cinchona quinine, comfrey, rosemary, Tote, gulfweed and the like.

Of these, L-ascorbic acid, arbutin, kojic acid, placenta extracts, chamomile extract, tea plant extract, the extract of the root of kudzu and licorice extract are particularly preferred.

These anti-melanogenic agents may be used either singly or in any combination thereof and are preferably incorporated in a proportion of 0.01–10%, particularly 0.1–5% (in terms of dry solids content in the case of a plant extract) based on the total weight of the composition.

The sebum secretion inhibitors serve to prevent pigmentation and skin roughness around pores of the skin, pimple and the like caused by hypersteatosis, and as such agents, may be used, for example, anti-androgenic agents, crude drug extracts, astringents and the like, which are printed in "Fragrance Journal, Vol. 10 (1994)" and are in common use as sebum secretion inhibitors.

Specifically, examples of the anti-androgenic agents include oxendolone, 17-α-methyl-β-nortestosterone, chlormadinone acetate, cyproterone acetate, spironolactone, hydroxyflutamide, estradiol and ethinyl estradiol.

Examples of the crude drug extracts include extracts from leaves of walnut, *Scutellariae radix*, sage, hop, rosemary, Saint-John's-wort, Japanese mint, chamomile, cashew, goldthread, Amur cork tree, *Scutellaria balculensis* Georgi (Labiatee), *houttayniae herba*, dried orange peel, carrot, peony, Mat Rush, propolis, *alismatis rhizome*, tannin, hamanelis, peony and birch tar, and royal jelly and yeast extract.

Examples of the astringents include zinc sulfocarbolate, zinc oxide, aluminum hydroxychloride and (allantoinato) dihydroxyaluminum.

Vitamin $B_6$, 13-cis-retinoic acid, vitamin E, glycyrrhetinic acid, salicylic acid, nicotinic acid, calcium pantothenate, dicalcium azelate, 10-hydroxy-undecanoic acid, 12-hydroxystearic acid and the like may also be used as sebum secretion inhibitors.

These sebum secretion inhibitors may be used either singly or in any combination thereof and are preferably incorporated in a proportion of 0.01–10%, particularly 0.1–5% (in terms of dry solids content in the case of a crude drug extract) based on the total weight of the composition.

Any agent may be used as the blood circulation-facilitating agent used in the present invention so far as it is an ingredient commonly used in the classical cosmetic compositions, quasi-drugs and drugs. For example, a simple compound, plant extract or the like may be used without any particular limitation.

Specifically, examples of the compound include esterified products, nicotinate and orotate of vitamin E, which are described as vasodilators in Japanese Patent Application Laid-Open No. 87506/1987; esterified products, acetate and succinate of vitamin E, which are described as periphery circulation-facilitating agents in Japanese Patent Application Laid-Open No. 195316/1987; and besides nicotinic acid amide, methyl nicotinate and the like. Examples of the plant extract include plant extracts which are clearly described as having a blood circulation-facilitating effect in "Fragrance Journal, Extra Edition Vol. 6 (1986)" and "Fragrance Journal, Extra Edition Vol. 1 (1979)", for example, extracts from arnica, hawthorn, cinchona quinine, Scarlet sage, *Tilia europaea L*, Panax Ginseng C.A. Meyer, juniper, rosemary, Saint-John's-wort, ginkgo, melissa, *Ononis spinosa L*, marronnier, Japanese green gentian, garlic, chamomile, Japanese mint, nettle, red pepper, ginger, hop, horse chestnut, lavender, carrot, brown mustard, cinnamon, pine, *Cnidium ooficinale Makino*, elder, Japanese parsley, *Scoploia japonica Maxim*, peony, myrica, *Houttaynia cordata*, candock, astringent persimmon, pot marigold field poppy, gentian, grapes, *Glehnia littoralis*, bitter orange, citron, calamus, Watson pomelo, hamamelis, melilot, fennel, Japanese pepper tree, peony, eucalyptus, mugwort, *Isodon Japonicus Hara*, rice, *Sophoa flarescence Aiton*, zingiber, clove, Japanese linden and rice germ.

These blood circulation-facilitating agents may be used either singly or in any combination thereof and are preferably incorporated in a proportion of 0.001–5%, more preferably 0.01–3%, most preferably 0.02–2% based on the total weight of the composition, because a cosmetic composition having a sufficient effect for improving a complexion and giving no feeling of glow can be provided. Incidentally, in the case of the plant extract, the incorporated amount in terms of dry solids content should preferably fall within the above range.

No particular limitation is imposed on the moisturizers. However, examples thereof include ethylene glycol, diethylene glycol, triethylene glycol and still higher polyethylene glycols; propylene glycol, dipropylene glycol and still higher polypropylene glycols; butylene glycols such as 1,3-butylene glycol and 1,4-butylene glycol; glycerol, diglycerol and still higher polyglycerols; sugar alcohols such as sorbitol, mannitol, xylitol and maltitol; adducts of glycerols with ethylene oxide (hereinafter abbreviated as "EO") or propylene oxide (hereinafter abbreviated as "PO"); adducts of sugar alcohols with EO or PO; monosaccharides such as galactose and fructose, and EO or PO addicts thereof; polysaccharides such as maltose and lactose, and EO or PO addicts thereof; sodium pyrrolidonecarboxylate; and polyoxyethylene methylglucosides (number of moles of EO added: 10, 20, etc.).

Examples of the softeners include α-hydroxy acids such as α-hydroxyisobutyric acid, α-hydroxyisocaproic acid, α-hydroxy-n-capronic acid, α-hydroxyisocaprylic acid, α-hydroxy-n-caprylic acid, α-hydroxy-n-capric acid, lactic acid, α-hydroxystearic acid, citric acid and glycolic acid; basic amino acids such as lysine, arginine, histidine, omithine and canavanine; amines such as ε-aminocaproic acid, urea, 2-hydroxyquanidine and 2-(2-hydroxyethoxy) ethylguanidine; and beside peptides described in Japanese Patent Application Laid-Open Nos. 99315/1987 and 178207/1990, and trimethylglycine described in Japanese Patent Application Laid-Open No. 293625/1994.

As the surfactant, any of nonionic surfactants, anionic surfactants, cationic surfactants and amphoteric surfactants may be used without any particular limitation. However, examples thereof include polyoxyethylene (hereinafter abbreviated as "POE") hardened castor oil, POE alkyl ethers, POE branched alkyl ethers, POE fatty acid esters, POE glycerol fatty acid esters, POE sorbitan fatty acid esters, POE sorbitol fatty acid esters, POE hardened castor esters, POE alkylsulfates, POE alkyl sulfates, polyglycerol fatty acid esters, alkyl phosphates, POE alkyl phosphates, alkali metal salts of fatty acids, sorbitan fatty acid esters, glycerol fatty acid esters, alkyl polyglucosides, polyethylene glycol fatty acid esters, a-monoisostearyl glyceryl ether, sodium stearoyl methyltaurine, sodium POE lauryl ether phosphate and ether-modified silicones.

No particular limitation is imposed on the keratin protecting agents. However, examples thereof include mucopolysaccharides such as hyaluronic acid and chondroitin sulfate, proteins such as gelatin and collagen, and acid hetero-polysaccharides described in Japanese Pat. No. Application Laid-Open No. 10997/1989.

No particular limitation is imposed on the thickeners. However, examples thereof include high molecular compounds such as carrageenan, dextrin, methyl cellulose, ethyl cellulose, hydroxyethyl cellulose, hydroxypropyl cellulose, hydroxypropyl methylcellulose, polyvinyl alcohol, polyacrylic acid, sodium polyacrylate, polymethacrylic acid, carboxyvinyl polymers, xanthan gum, carboxymethylchitin, chitosan, SEPAGEL-305 ™ by Seppic, a mixture of laureth-7, polyacrylamide and $C_{13-14}$ isoparaffin, and cationized cellulose, and inorganic compounds such as aluminum magnesium silicate, kaolin and bentonite.

The cosmetic compositions according to the present invention may be provided as oil-based cosmetic compositions, liquid crystal type cosmetic compositions or the like in any form of liquid, solid, paste, jelly, and the like. They may also be provided as compositions of such a type as after being applied, that they are washed out after massaging, or that they are wiped out after massaging.

In the present invention, it goes without saying that taking the content of a solvent used as a base, for example, an alcohol, into consideration upon incorporation of the disintegrating granules, disintegrating granules, which are not disintegrated by such a solvent, are chosen for use.

The anhydrous self-indicating cosmetic composition may be formulated as a cleansing composition and used to cleans facial skin, as a facial mask, body skin, as a body scrub, or foot skin, as a foot scrub. More specific cosmetic cleansing compositions may be formulated for each of these specific skin cleansing applications. For example the concentration of self-indicating disintegrating granules may be increased for a foot cleansing composition to account for the diminished sensitivity of the skin, relative to facial skin. In addition, self-indicating disintegrating granules used in a foot cleansing composition may be of a higher compression strength and/or larger primary particle size, than those used in a facial composition. The addition of an antibacterial agent such as triclosan may be advantageous to body and/or foot scrub compositions. The addition of an antifungal agent may be particularly advantageous to a foot scrub composition.

The cosmetic composition may also be formulated as a moisturizing composition. The necessary components for formulating a moisturizing composition will be appreciated by those of ordinary skill in the art. Moisturizing compounds known to those of ordinary skill in the art include shea butter, stearyl dimethicone, and $C_{10-30}$ cholesterol/lanosterol esters.

The cosmetic compositions according to the present invention may be used by applying them to moistened skin, such as that of the face, neck and/or the like by the conventional method followed by manual massaging after application or inunction of the composition.

For massaging or inunction, it is only necessary to take a necessary amount, for example, 1–10 g, of the composition in user's hand, lightly apply it to moistened skin, such as the face, neck and/or the like, lightly massage the part applied with the palm of the hand or the inner surfaces of fingers until a nearly uniform color is achieved (about 30–60 seconds), and wipe the composition out with a tissue or cotton or wash it out with water or hot water.

The present invention is an improvement over the prior art in that it provides for a color change which occurs at the same time as the heat is released. The benefit of the color change is to provide a signal to the user that they have achieved optimal contact between the anhydrous composition and water. This will ensure that heating effect will be maximized since the release of heat is triggered by intimate contact between the cosmetic composition and water. The color, which is preferably a water-dispersible colorant, is contained within small beads which are included in the composition with a self-heating component. The beads containing the coloring agent also provide a mild abrasive effect during use.

In summary, the present invention is an improved cosmetic composition which is intended to be applied to wet skin. The cosmetic composition is composed primarily of 1) a heat-generating component which releases heat when brought into contact with water, preferably Zeolite A, 2) a bead containing a water-dispersible colorant where the bead is sufficiently friable that it breaks down when rubbed onto wet skin, and 3) an anhydrous water-miscible vehicle such as propylene glycol or butylene glycol.

Obviously, numerous modifications and variations of the present invention are possible in light of the above teachings. It is therefore to be understood that within the scope of the appended claims, the invention may be practiced otherwise than as specifically described herein.

EXAMPLE 1

| Part | Material Description: | Formula % WW |
|---|---|---|
| A: LIQUID PHASE | Propylene Glycol | q.s. to 100% |
| | PEG-8 | 4.08 |
| | Methyl gluceth-20 | 2.04 |
| | Glycerin | 2.04 |
| | Dimethicone | 1.00 |
| B: SOLIDS PHASE | Kaolin | 16.05 |
| | Sodium Aluminosilicate | 38.20 |
| | Silica | 1.00 |
| | Hydroxypropyl Methylcellulose | 0.65 |
| | Talc | 1.00 |
| C: Color Indicating Beads | Polyethylene/colorant/ Hydroxypropylcellulose | 0.80 |
| D: Scrub Beads | Acrylates Copolymer | 0.70 |
| E. Fragrance | Fragrance | 0.10 |

EXAMPLE 2

Self-indicating disintegrating granules were prepared from polyethylene particles, ultramarines colorant and hydroxypropyl celluose as binder as follows:

| % | A | B | C |
|---|---|---|---|
| Polyethylene beads | 85 | 83 | 79 |
| Ultramarines | 9 | 9 | 9 |
| hydroxypropyl cellulose | 6 | 8 | 12 |
| Total | 100 | 100 | 100 |

Polyethylene beads and ultramarines pigment were mixed, followed by addition of hydroxypropyl cellulose to form a slurry. Granules were formed upon drying, wherein rough granules were sorted by mesh to obtained the desired particle size.

EXAMPLE 3

In order to test the affect of self-indicating disintegrating bead loading amounts on color indication, the following experiments were conducted.

| % | A | B | C | D | E | F |
|---|---|---|---|---|---|---|
| 1,3 butylene glycol | 44.9 | 44.7 | 44.5 | 44.3 | 44.1 | 43.0 |
| Kaolin | 15.0 | 15.0 | 15.0 | 15.0 | 15.0 | 15.0 |
| Sodium Aluminosilicate | 40.0 | 40.0 | 40.0 | 40.0 | 40.0 | 0.0 |
| Polyethylene beads/HPC/ Colorant* | 0.1 | 0.3 | 0.5 | 0.7 | 0.9 | 2.0 |
| Total | 100.0 | 100.0 | 100.0 | 100.0 | 100.0 | 100.0 |

*MPG blue beads of Example 2A 1 g of each of the samples A–F described above were applied onto the palm of panelist hands. Each panelist rubbed the palm with their finger for 1 minute. The observed appearance after 1 minute was recorded.

| | Results |
|---|---|
| Sample A | Color change was too subtle to detect |
| Sample B | Color change was noticeable but weak |
| Sample C | Color change was noticeable. |
| Sample D | Color change was noticeable |
| Sample E | Color change was noticeable but left unbroken beads |
| Sample F | Color change was noticeable but left many unbroken beads |

EXAMPLE 4

| Formula preparation | | |
|---|---|---|
| Part A | Propylene glycol | 38.00 |
| | Glycerine | 2.40 |
| | PEG 8 | 8.00 |
| | BHT | 0.10 |
| | Hydroxypropyl methyl celluose | 0.50 |
| Part B | Sodium Aluminosilicate | 37.00 |
| | Kaolin | 12.00 |
| Part C | Fragrance | 0.20 |
| Part D | Acrylates copolymer | 0.80 |
| | Polyethylene/Colorant/hydroxypropyl cellulose | 1.00 |

The components of Part A were heated to 70–80° C., to dissolve BHT and activate the hydroxypropyl cellulose polymer. Sodium Aluminosilicate was sprinked into the liquid, and then a vacuum was pulled. Glycerin and PEG-8 were introduced under vacuum. The vacuum was broken and kaolin was added to the mixture, followed by reintroduction of the vacuum. The mixture was cooled to 30–40° C. under vacuum. The vacuum was broken and fragrance added. A vacuum was pulled again, and beads were sucked up into the mixture of ABC, with agitation on. Excessive mixing was avoided to avoid premature color release.

EXAMPLE 5

| % | A | B | C | D |
|---|---|---|---|---|
| Propylene glycol | 35.50 | — | 25.00 | 30.00 |
| Butylene glycol | — | 35.00 | 10.00 | 5.00 |
| Glycerine | — | 4.00 | 3.00 | 1.60 |
| PEG-8 | 6.0 | 5.00 | 3.00 | 4.50 |
| Dimethicone | — | 2.30 | 3.04 | 1.00 |
| Methyl gluceth-20 | 0.05 | 0.05 | 0.05 | 0.05 |
| Tetrasodium EDTA | 40.00 | 38.00 | 36.00 | 42.00 |
| Sodium Silicoaluminate | 40.00 | 38.00 | 36.00 | 42.00 |
| Kaolin | 15.00 | 12.00 | 14.00 | 10.00 |
| Talc | 1.00 | 1.50 | 1.70 | 2.05 |
| Acrylates Copolymer | 0.50 | 0.40 | 1.60 | 0.30 |
| Polyethylene/Colorant/ hydroxypropyl cellulose | 0.50 | 0.30 | 0.90 | 0.70 |
| hydroxypropyl cellulose | 0.50 | 0.30 | 0.40 | 0.60 |
| hydroxmethyl cellulose | 0.25 | 0.65 | 0.30 | 0.40 |
| BHT | 0.10 | 0.10 | 0.10 | 0.05 |
| Fragrance | 0.10 | 0.20 | 0.10 | 0.25 |
| Total | 100.00 | 100.00 | 100.00 | 100.00 |

EXAMPLE 6

Moisturizing Mask Example

| Part | Material Description | |
|---|---|---|
| A: Liquid Phase | Butylene Glycol | q.s. to 100% |
| | PEG-8 | 4.00 |
| | Tetrasodium EDTA (39%) | 0.01 |
| B: Solid Phase | Sodium Silicoaluminate | 36.00 |
| | Titanium Dioxide | 0.50 |
| | BHT | 0.01 |
| | Hydroxypropyl Methylcellulose | 0.20 |

-continued

| Part | Material Description | |
|---|---|---|
| C: Emollient Phase | Shea Butter | 4.00 |
| | Stearyl Dimethicone | 0.50 |
| | Polyacrylamide (and) $C_{13-14}$ Isoparaffin (and) Laureth-7 | 1.75 |
| | $C_{10-30}$ Cholesterol/Lanosterol Esters | 1.00 |
| D: Color Indicating Beads | Polyethylene/ultramarines/ Hydroxypropylcellulose | 0.80 |
| E: Fragrance | Fragrance | 0.1 |

Obviously, numerous modifications and variations of the present invention are possible in light of the above teachings. It is therefore to be understood that within the scope of the appended claims, the invention may be practiced otherwise than as specifically described herein.

What is claimed is:

1. A non-oil based anhydrous cosmetic composition comprising:
    i) an anhydrous self-heating component that releases heat when brought into contact with water;
    ii) self-indicating disintegrating granules comprising:
        a) a water-insoluble polymer; and
        b) a colorant; and
    iii) an anhydrous water-miscible vehicle;
wherein said composition contains no more than 5 wt % water.

2. The cosmetic composition according to claim 1, wherein said disintegrating granules before incorporated in the cosmetic composition have a compression strength of 0.01–0.5 kgf/mm and a particle size of 100–2,000 μm, and the primary particles thereof have an average particle size of at most 100 μm.

3. The cosmetic composition of claim 1, wherein said self-indicating disintegrating granules further comprises a binder.

4. The cosmetic composition of claim 3, wherein said binder is comprised of a water-soluble binder.

5. The cosmetic composition according to claim 1, wherein said water-insoluble polymer is selected from the group consisting of polyethylene, polystyrene, polyester, polyvinyl chloride, polyamide, polypropylene, nylon, polyvinylidene fluoride, polyurethane, acrylic resins, polysiloxane, crystalline cellulose, starch and derivatives thereof, silica, alumina, talc, kaolin, titanium oxide, zinc oxide, quartz and calcium phosphate.

6. The cosmetic composition according to claim 3, wherein said binder is selected from the group consisting of ethyl cellulose, acetyl cellulose, nitrocellulose, hydroxymethyl cellulose, hydroxyethyl cellulose, hydroxypropyl cellulose, polyvinyl pyrrolidone, polyvinyl acetate and polyvinyl alcohol.

7. The cosmetic composition according to claim 3, wherein said water-insoluble polymer is comprised of polyethylene, and said binder comprises hydroxypropyl cellulose.

8. The cosmetic composition according to claim 3, wherein said self-indicating disintegrating granules are incorporated in an amount of 0.1–5 wt. % based on the total weight of the composition.

9. The cosmetic composition of claim 1, wherein said anhydrous water-miscible vehicle is selected from the group consisting of ethylene glycol, diethylene glycol, triethylene glycol, polyethylene glycol; propylene glycol, dipropylene glycol, polypropylene glycol; butylene glycol, glycerol, diglycerol, higher polyglycerols; sugar alcohols, adducts of glycerols with ethylene oxide or propylene oxide; adducts of sugar alcohols with ethylene oxide or propylene oxide; galactose, fructose, ethylene oxide adducts of galactose, propylene oxide adducts of galactose, ethylene oxide adducts of fructose, propylene oxide adducts of fructose, maltose, lactose, sodium pyrrolidonecarboxylate, polyoxyethylene methylglucosides and a mixture thereof.

10. The cosmetic composition of claim 1, wherein said anhydrous water-miscible vehicle comprises butylene glycol.

11. The cosmetic composition of claim 1, wherein said composition is a cleansing composition.

12. The method of claim 1, wherein said composition is a moisturizing composition.

13. The cosmetic composition of claim 1, wherein said composition comprises ≦2.5 wt. % water, if any.

14. The cosmetic composition of claim 1, wherein said composition comprises ≦1.0 wt. % water, if any.

15. The cosmetic composition of claim 1, wherein said self-indicating disintegrating granules are comprised of primary particle of water-insoluble polymer, a colorant and a binder.

16. The cosmetic composition of claim 1, wherein said self-indicating disintegrating granules are comprised of a matrix of water-insoluble polymer in which colorant is entrapped.

17. A method comprising sequentially:
  i) moistening skin;
  ii) applying the cosmetic composition of claim 1 to said moistened skin;
  iii) physically manipulating said cosmetic composition;
  iv) detecting a color change in said cosmetic composition; and
  v) removing said cosmetic composition.

18. The method of claim 17, wherein said skin is facial skin.

19. The method of claim 17, wherein said skin is foot skin.

20. The method of claim 17, wherein said skin is body skin other than facial skin.

* * * * *